United States Patent [19]
Gipson

[11] 3,954,873
[45] May 4, 1976

[54] AMINO ALCOHOLS

[75] Inventor: Robert M. Gipson, Austin, Tex.

[73] Assignee: Robert M. Gipson, Houston, Tex.

[22] Filed: Apr. 17, 1974

[21] Appl. No.: 461,549

Related U.S. Application Data

[62] Division of Ser. No. 263,552, June 16, 1972, Pat. No. 3,872,116.

[52] U.S. Cl. ............... 260/584 R; 252/392; 260/247.7 Z; 260/268 R; 260/348 R; 260/534 M; 260/534 R; 260/570.9; 260/573; 260/583 P; 424/325; 424/330
[51] Int. Cl.² .................................. C07C 91/04
[58] Field of Search ........ 260/584 R, 534 M, 583 P, 260/573

[56] References Cited
UNITED STATES PATENTS

| | | | |
|---|---|---|---|
| 3,200,153 | 8/1965 | Kirkpatrick et al. | 260/584 R |
| 3,200,154 | 8/1965 | Kirkpatrick et al. | 260/584 R |
| 3,203,981 | 8/1965 | Hargrove | 260/584 R |

OTHER PUBLICATIONS
Hayashi et al. Chem. Pharm. Bull. (Japan) 17(1), 1969, pp. 145–149.

*Primary Examiner*—Arthur P. Demers
*Attorney, Agent, or Firm*—John R. Kirk, Jr.; Terrence Dean Dreyer; James L. Bailey

[57] ABSTRACT

Compounds of the formulas

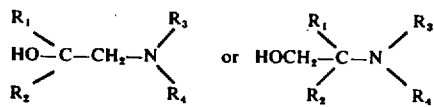

including particular derivatives thereof, are provided. The subject compositions have utility in a wide variety of applications and their use as corrosion inhibitors for metals is exemplary.

2 Claims, No Drawings

AMINO ALCOHOLS

This is a division of application Ser. No. 263,552, filed June 16, 1972, now U.S. Pat. No. 3,872,116.

BACKGROUND OF THE INVENTION

1. Field of the Invention

The invention pertains to new organic chemicals.

2. Description of the Prior Art

John Gerecht's U.S. Pat. No. 3,547,932 (1970) discloses the compounds N-2-hydroxyalkyl piperidine or pyrrolidine and their corresponding oxides. Howard Drew's U.S. Pat. No. 3,441,612 (1969) also discloses hydroxyalkyl amine oxides.

SUMMARY OF THE INVENTION

The invention is amino alcohols (which includes the salts, such as the sulfates, hydrochlorides, and the like; quaternary ammonium compounds; alkylene oxides; and amine oxides derived therefrom) of the formulas I or II

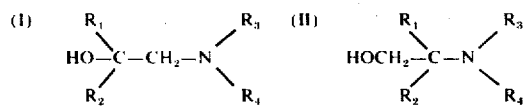

wherein, individually, $R_1$ and $R_2$ are linear $C_1$–$C_{36}$ alkyl groups, preferably $C_4$–$C_{18}$, alkyl groups and $R_1$ and $R_2$ contain a total of 8 to 38 carbon atoms; individually, $R_3$ and $R_4$ are (a) hydrogen or (b) are selected from alkyl, aryl, aralkyl, or alkaryl radicals, each radical containing from 1 to 10 carbon atoms or (c) where $R_3$ and $R_4$ are joined together to form a morpholine or piperazine ring; or (d) are the radical $-(CH_2)_m-[HN-(CH_2)_m-]_n-Z$, wherein $m$ is 2 or 3, $n$ is 1 to 3 and Z is $-NH_2$ or $-OH$; and wherein the alkyl or aryl groups, or combinations thereof, comprising $R_3$ or $R_4$ individually can be substituted alkyl or substituted aryl groups containing hydroxyl, ether, amino, or carboxyl substituents, or admixtures thereof. For example, individually, $R_3$ and $R_4$ can be selected from $-CH_2-CH_2-NH_2$, $-CH_2-CH_2-OH$,

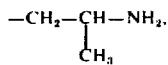

$-CH_2-CH_2-O-CH_2-CH_2OH$,

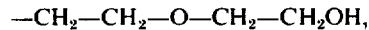

$-CH_2-\emptyset$, or $-CH_2-CH_2-NH-CH_2-CH_2-NH_2$, and the like. Preferably, $R_3$ and $R_4$ are individually selected from methyl, ethyl, hydroxyethyl, hydroxypropyl, aminoethyl, aminopropyl, or benzyl radicals.

DESCRIPTION OF THE PREFERRED EMBODIMENTS

The amino alcohols of the invention are prepared by reacting epoxides of formula III

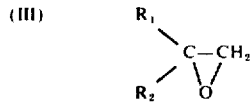

with amines of formula IV

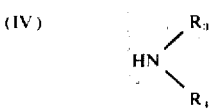

wherein $R_1$, $R_2$, $R_3$ and $R_4$ are as defined in the summary of the invention, above.

Exemplary amines of formula IV include, for example, ammonia, methylamine; dimethylamine; diethylamine; dipropylamine; dibutylamine; ethylenediamine; 1,3-propanediamine; diethylenetriamine; triethylenetetramine; hexaethyleneheptamine; imino-bis-propylamine; ethanolamine; diethanolamine; aminoethylethanolamine; aniline, benzylamine; piperazine; morpholine; and the like.

Suitable epoxides conforming to the above formula III can be prepared according to copending U.S. Patent application Ser. No. 263,678, filed June 16, 1972, now U.S. Pat. No. 3,835,166, entitled "2,2-Dialkylepoxides," by Robert M. Gipson et al., which disclosure is incorporated herein by reference thereto.

As hereinbefore stated, my invention includes the salts, quaternary ammonium compounds, alkylene oxides, and the amino oxides that are derived from particular amino alcohol compositions of this invention.

In most instances these derivatives can be prepared directly, i.e., without having to perform a separate recovery step to isolate the amino alcohols of this invention. It is sometimes preferable, however, to separate the amino alcohol products of this invention before proceeding to prepare these derivatives of my invention as hereinafter described.

The novel alkylene oxide compositions of this invention are derived by reacting alkylene oxides that contain preferably from two to four carbon atoms per molecule with certain amino alcohols of this invention that conform to formulas I or II above provided however that at least one of said $R_3$ or $R_4$, as hereinbefore defined, is the radical $-(CH_2)_m-[HN-(CH_2)_m]_n-Z$, wherein $m$, $n$ and Z are as hereinbefore defined. Preferably, one of $R_3$ or $R_4$ is hydrogen.

Accordingly, alkylene oxide compositions are provided that conform to the following illustrative formulas

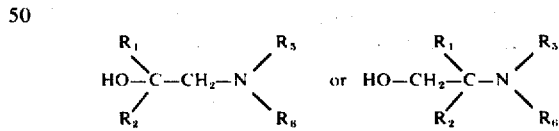

wherein, individually, $R_5$ or $R_6$ are (a) the same as $R_3$ or $R_4$, as hereinbefore defined except that $R_5$ and $R_6$ are not hydrogen, or (b)

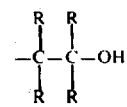

and provided that at least one of $R_5$ or $R_6$ is

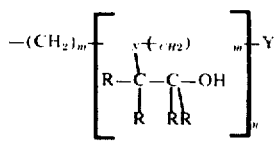

where R is hydrogen or a lower alkyl, e.g., $C_1$–$C_4$, and $m$ and $n$ are as hereinbefore defined, and Y is (1) 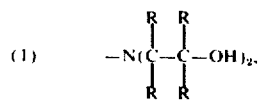 (2) 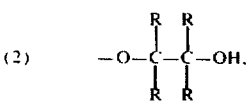

and wherein R is as previously defined.

Alkylene oxides such as ethylene oxide; propylene oxide; isobutylene oxide; 1,2-epoxybutane; 2,3-epoxybutane; or admixtures thereof; are represenative of preferred oxides useful in preparing our novel alkylene oxide compositions. The alkoxylation reaction can be conducted using conventional methods and conditions such as temperatures within the range of about 40° to 200°C, and pressures from about 0 to 100 psig. Representative procedures are described in the following reference which disclosure is incorporated herein by reference thereto. Martin J. Schick, Ed., *Nonionic Surfactants*, Marcel Dekker Inc., New York, 1967, pp 187–204.

Likewise, novel amine oxide compositions are provided which can be illustrated by the formulas

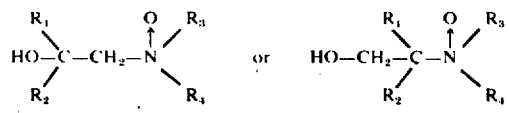

wherein $R_1$, $R_2$, $R_3$ and $R_4$ are as heretofore defined except that $R_3$ and $R_4$ are not hydrogen. Accordingly, the novel amino alcohols from which the novel amine oxide compositions are derived are prepared using an amino alcohol of formulas I or II provided however that $R_3$ and $R_4$ are other than hydrogen. Conventional procedures can be used to form the amine oxides such as procedures represented by D. B. Luke and G. L. K. Hah, J. Am. Oil Chem. Soc., 40, 628 (1963), which disclosure is hereby incorporated by reference thereto.

The novel quaternary ammonium compounds that are derived from my amino alcohols can be illustrated by the following representative formulas

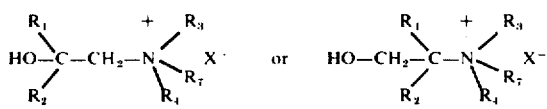

wherein $R_1$, $R_2$, $R_3$ and $R_4$ are as previously defined, and $R_7$ represents (a) a $C_1$–$C_5$ saturated or unsaturated aliphatic hydrocarbon radical such as ethyl, butyl, allyl, and the like, (b) an aromatic hydrocarbon radical containing from 6 to 14 carbon atoms per radical, such as phenyl, benzyl, and the like, or substituted radicals of (a) or (b) having substituents thereon selected from hydroxyl, amino, ether or carboxyl, and admixtures thereof; and wherein X represents an anion such as the halides, e.g., chloride, bromide; hydroxide; methylsulfate; and the like.

The quaternary ammonium compounds of this invention can be prepared from my novel amino alcohols by conventional methods and conditions. For example, alkylating agents such as the primary halides, e.g., methylbromode, benzylchloride, or the like; dialkylsulfates, ethylene oxide; chloroacetic acid and the like, can be suitably employed for reacting with the amino alcohols of formulas I and II to provide quaternary compounds of this invention. A representative preparation of quaternary ammonium compounds is described by Melvin J. Astle, Ed., *Industrial Organic Nitrogen Compounds*, Rheinhold Pub. Corp., N.Y., 1961, which disclosure is incorporated herein by reference thereto.

The amino alcohols of this invention, as well as the amine oxides; alkylene oxides; and quaternary compounds derived therefrom, are useful as corrosion inhibitors for metals. The amino alcohols are also useful in preparing amphoteric compounds which demonstrate significant surfactant activities.

Likewise, the amine oxides, alkylene oxides, and quarternary ammonium compounds also demonstrate useful surfactant characteristics. Particular compositons have also been found to exhibit biological activities.

Unexpectedly, the activity characteristics of our compositions are such that they can be conveniently and advantageously utilized in widely varied applicatons. Also in view of the essentially linear nature of our compositions it was particularly astounding to discover that our compositions had extremely low freezing points and that they were essentially completely soluble in organic solvents. The amino alcohols of formulas I and II, for example, are soluble in essentially all conventional organic solvents.

As herein described, novel amino alcohols are provided by reacting the epoxides of formula III with the amines of formula IV. Generally, this reaction can be conducted at temperatures within the range of about 60° to 200°C, preferably from about 80° to 180°C. Times in the range of about 10 minutes to 72 hours can be employed and generally about 30 minutes to 10 hours is suitable. Pressures that are sufficient to maintain the reactants and products essentially in the liquid phase are preferred. If desired, an inert or nonoxidizing atmosphere can be maintained such as by employing nitrogen, methane, or the like in the reaction vessel. Aromatic and aliphatic solvents such as the alcohols, e.g., methanol, isopropyl-alcohol, and the like; ether; or chlorobenzene, and the like, can be conveniently employed although solvents are not required.

Although no catalyst is strictly necessary, mineral acid and halide acid salts of the amines of formula IV are suitable catalysts for the reaction between the epoxides and amines of formulas III and IV respectively. Thus, preformed acid salts can be suitably employed or the catalyst can be formed in situ by the addition of the mineral acid or halide acid, or admixtures thereof, to the vessel containing the reactants, i.e., the compounds of formulas III and IV.

Mineral acids suitable for in situ catalyst preparation or for use in preforming the mineral acid salts of the stated amines are hydrochloric acid, sulfuric acid, and the like. Representative halide acids are HBr, HCl, HI, and the like.

Exemplary preformed acid salt catalysts are dimethylamine hydrochloride, ethanolamine bisulfate, triethanolamine hydrochloride, and the like.

Other preferred catalysts that can be suitably employed for preparing the subject amino alcohols include the Lewis acids. Exemplary are boron trifluoride, titanium tetrachloride, aluminum chloride, tin tetrachloride, and the like.

Other catalysts such as quaternary ammonium salts can also be used. Exemplary are as tetramethylammonium chloride, trimethyllauryl ammonium chloride, tetraethylammonium bromide, and the like. Alkali metal alkoxides formed from lower alkyls, e.g., $C_1$ to $C_4$, such as sodium methoxide are another class of suitable catalysts. The mineral acid salts and the halide acid salts of the stated amines and the Lewis acids are the preferred catalytic material.

Although the amount of catalyst or catalysts used can vary widely, generally from about 0.00001 to 1.0 mol of the catalyst is provided per each mol of the amine compound (i.e., composition represented by formula IV).

Generally, the amine compound of formula IV is employed in an amount such that about 0.1 to 10 mols of said amine compound is provided for each mol of said epoxide compound of formula III. For convenient and economic processes, generally about stoichiometric quantities of the two reactants as represented by formulas III and IV are employed.

Illustrative of the foregoing discussion and description, and not to be interpreted as a limitation on the scope thereof or on the materials herein employed, the following examples are presented.

EXAMPLE 1

A 250 ml three neck flask equipped with a stirrer, thermometer and reflux condenser was charged with 100 g morpholine, 4 ml concentrated hydrochloric acid and 50 g of a mixture of 1,2-epoxy-2-octyldecane and 1,2-epoxy-2-hexyldodecane. This mixture was stirred and heated at reflux (128°–30°C) for 20 hours. The reaction mixture was diluted with 300 ml benzene. This solution was washed twice with 200 ml 5% sodium hydroxide, dried over sodium sulfate and the benzene and excess morpholine removed in vacuo to give 61 g product. The infrared and nuclear magnetic resonance spectra showed the material obtained was predominately compounds of the formulas

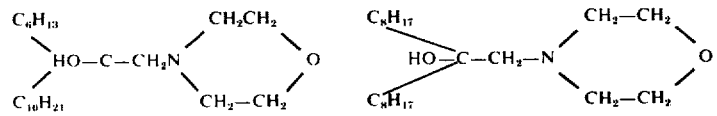

EXAMPLE 2

A one liter stirred autoclave was charged with 100 g of epoxide consisting essentially of 1,2-epoxy-2-hexyldecane, 3 g tetraethylammonium bromide, 300 g tertiary butyl alcohol and 100 g ammonia. The autoclave was stirred and heated to 178°–82°C for 3.75 hours. The pressure dropped from 1400 to 1040 psig during this period. The effluent was stripped of alcohol and the residue dissolved in 200 ml benzene. This solution was washed twice with 100 ml of water, dried over sodium sulfate, filtered, and the benzene removed in vacuo to give 98 g product. The product contained 2.92 milliequivalents per gram amine by titration. The infrared and nuclear magnetic resonance spectra showed the product to be a mixture of amines of the formulas

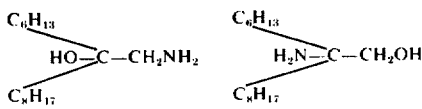

EXAMPLE 3

A one liter stirred autoclave was charged with 150 g ethylenediamine, 100 g epoxide consisting essentially of 1,2-epoxy-2-butyloctane and 3 ml concentrated hydrochloric acid. The autoclave was pressured to 100 psig with nitrogen and heated at 160°C for 4 hours. The reactor effluent was diluted with 150 ml benzene. The resulting solution was washed twice with 5% sodium hydroxide and once with water. The benzene was stripped and the residue distilled to give 95 g material, b.p. 140°C at 0.5 mm Hg. The product contained 8.23 milliequivalents per gram amine (theory=8.20) and 4.06 milliequivalents per gram primary amine (theory=4.10). The infrared and nuclear magnetic resonance spectra showed that the product was predominantly a compound of the formula

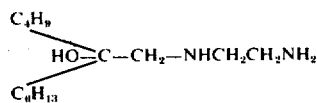

EXAMPLE 4

A one liter stirred autoclave was charged with 100 g 1,2-epoxy-2-octyldodecane, 100 g dimethylamine, 3 g tetraethylammonium bromide, and 300 g t-butyl alcohol. The autoclave was pressured to 200 psig with nitrogen and heated at 160°C for 4 hours. The effluent was stripped of alcohol and 200 ml benzene added to the residue. This mixture was filtered. The filtrate was washed twice with 100 ml 5% sodium chloride solution, dried over sodium sulfate, filtered and the benzene removed in vacuo to give 95 g of product. The product contained 2.70 milliequivalents per gram amine. The infrared and nuclear magnetic resonance spectra showed that the material was predominantly a compound of the formula

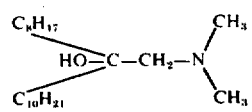

EXAMPLE 5

A one liter flask equipped with a stirrer and a condenser were charged with 150 g 1,2-epoxy-2-octyldodecane, 150 g diethylenetriamine and 5 ml concentrated hydrochloric acid. This mixture was stirred and heated at 160°C for 3 hours. The effluent was washed once with 100 ml of water and twice with 200 ml 5% sodium hydroxide, dried over sodium sulfate and filtered. The filtrate was passed through a wiped film evaporator at 160°C and 0.2 mm Hg pressure. The bottoms were reflashed at 250°C and 0.2 mm Hg to give 130 g overhead (product) and 41 g bottoms. The overhead contained 7.15 milliequivalents per gram amine. The infrared and nuclear magnetic resonance spectra showed that the product was predominantly a compound of the formula

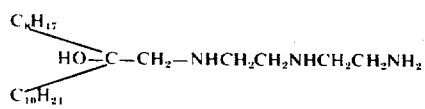

EXAMPLE 6

The product from Example 5 above was reacted with ethylene oxide at 120°–30°C to give a product containing 6.73 milliequivalents per gram hydroxyl groups and 4.73 milliequivalents per gram amine.

EXAMPLE 7

A 500 ml flask equipped with a stirrer, condenser and nitrogen purge was charged with 150 g of a mixture of 1,2-epoxy-2-hexyldodecane and 1,2-epoxy-2-octyldecane, 150 g diethanolamine, and 3 g ammonium chloride. This mixture was stirred and heated at 160°C for 4 hours. The reaction mixture was cooled and 100 ml benzene and 100 ml 5% sodium hydroxide solution were added. The organic layer was separated, washed three times with 100 ml 5% sodium hydroxide solution, dried over sodium sulfate, filtered, and stripped of benzene in vacuo to give 195 g viscous liquid product. The product contained 2.51 milliequivalents/g amine. The infrared and nuclear magnetic resonance spectra showed that the product was predominantly a mixture of compounds of the formulas

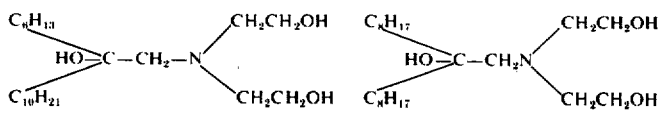

EXAMPLE 8

A 1 liter flask equipped with a stirrer, condenser, and thermometer was charged with 100 g imino-bis-propylamine, 100 g dichlorobenzene and 5 g ammonium chloride. This mixture was heated to 180°C and 100 g 1,2-epoxy-2-decyltetradecane was added over a 35-minute period. The temperature was maintained at reflux (187°–89°C) for an additional 1 hour. The reaction mixture was cooled to room temperature and 200 ml of 10% sodium hydroxide solution was added. The organic layer was separated, dried over sodium sulfate and filtered. The filtrate was passed through a wiped film evaporator at 200°C and 0.1 mm Hg pressure to remove solvent and unreacted starting material and give 109 g product (as bottoms). The product contained 5.03 milliequivalents/g amine. The infrared and nuclear magnetic resonance spectra showed that the product was predominantly a compound of the formula

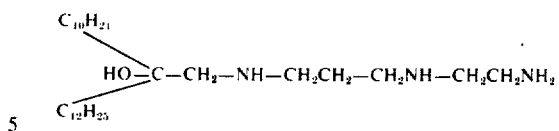

EXAMPLE 9

The product from Example 8 was reacted with ethylene oxide (excess), at 110°C to give a product containing 2.07 milliequivalents/g amine.

EXAMPLE 10

A flask was charged with 66 g triethylenetetramine, 1 ml concentrated hydrochloric acid and 200 g of a mixture 1,2-epoxy-2-hexyldodecane and 1,2-epoxy-2-octyldecane and the mixture heated at 150°C for 2 hours. After working up the mixture in a manner similar to that described in the above examples, 245 g of a mixture of mono- and dialkoxylated triethylenetetramine was obtained which contained 4.88 milliequivalents/g of amine.

EXAMPLE 11

A glass pressure bottle was charged with 20 g of the N,N-dimethylaminoalcohol of the formula

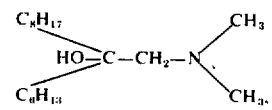

50 g pentane and 15 g methyl bromide. The reaction mixture was stirred and heated at 65°C for 3 hours. The bottle was cooled and vented. The precipitate was filtered, washed with pentane and dried to give 21 g of white crystalline material. Analysis for bromide (Volhard): found 20.6%; theory, 21.0%. The infrared and nuclear magnetic resonance spectra showed the structure to be a compound of the formula

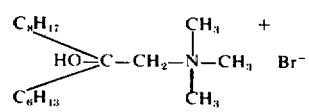

EXAMPLES 12–16

Some of the representative compositions that were likewise prepared according to the method of Example 11 include the following compositions which are described in illustrative fashion

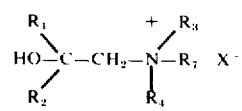

| Ex. No. | R₁ | R₂ | R₃ | R₄ | R₇ | X |
|---------|------|--------|--------|--------|--------|----|
| 12 | decyl | octyl | methyl | methyl | benzyl | Cl |
| 13 | octyl | hexyl | methyl | methyl | allyl | Cl |
| 14⁽¹⁾ a) | decyl | decyl | methyl | methyl | methyl | Br |
| b) | dodecyl | dodecyl | methyl | methyl | methyl | Br |
| 15⁽¹⁾ a) | octyl | octyl | methyl | methyl | methyl | Br |
| b) | decyl | hexyl | methyl | methyl | methyl | Br |
| 16 | octyl | hexyl | methyl | methyl | methyl | Cl |

⁽¹⁾50:50 wt. mixture of (a) and (b)

In further exemplification of our novel compositions and demonstrative of their varied activities the composition of Example 11 was tested for surface active properties. It was found to demonstrate a Draves wetting time of less than 1 second using a 1.5 gram hook at 0.25% concentration. The composition of Example 13 was tested for biological activity and found to be a post-emergent herbicide, a mildewcide against *erysiphe polgoni* and was also effective in inhibiting the growth of *staphylococcus aureus*. The composition of Example 14 was tested in the Ross Miles foam height test and demonstrated an initial foam height of 185 and a 5 minute foam height of 165. The composition of Example 15 demonstrated exceptional foaming power as determined by said Ross Miles test and demonstrated foam heights of 233 initial and 208 after 5 minutes. The Example 15 composition had a Draves wetting time of three seconds and 33 seconds at 0.1 and 0.05% concentration, respectively using a 3.0 gram hook. This composition also exhibited biological activity as a post emergent herbicide, mildewcide (both topical and systemic) and functioned as an aphicide. The composition of Example 16 was tested for metal corrosion inhibition and it was found effective.

EXAMPLE 17

A solution of 50 g of the amino alcohol of the formula

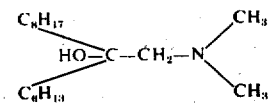

in 50 ml methanol, 25 ml 2-propanol and 20 ml water was stirred vigorously while 20 ml 50% hydrogen peroxide was added slowly thereto. The resulting mixture was stirred at 70°C for 3 hours and allowed to stand at room temperature for 48 hours. The excess hydrogen peroxide was destroyed by adding 0.5 g 5% platinum on carbon and stirring for 2 hours. The reaction mixture was filtered and the solvent removed at reduced pressure to give the amine oxide of the following formula containing only 0.03 milliequivalent/g free amine.

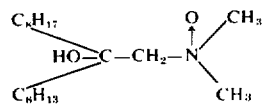

Results comparable to those disclosed in the examples are obtained when other compounds within the scope of the invention but not illustrated are prepared.

The compounds of the invention, as before stated, are useful in a variety of applications including usefulness as corrosion inhibitors for metals. In demonstration thereof, corrosion tests were carried out as follows. Test coupons of mild steel were buffed, washed with soap and water, rinsed in water, then acetone, and dried and weighed. The test coupons were placed in bottles containing the desired level of inhibitor, 14 ml kerosene and 70 ml synthetic brine (5.0% NaCl, 0.5% $CaCl_2$, 0.06% acetic acid, saturated with $CO_2$). A control with no inhibitor added was used in all tests. The bottles were placed on the outer perimeter of a 22 inch wheel which was turned at 37 rpm for 72 hours. The coupons were washed with soap and water, rinsed in water, then acetone, and dried and weighed. The percent protection given by the compounds of my invention was calculated by Wt. Loss of Control − Wt. Loss of Coupon/Wt. Loss of Control × 100%.

The compounds were tested as oleic acid salt (designated 0), acetic acid salt (designated A) or p-toluenesulfonic acid salt (designated T). These novel salts were prepared by neutralizing the amino alcohols of this invention with the respective acids. The higher temperatures employed in some runs were obtained by placing heat lamps in front of the rotating wheel. The test results are reported in Table I. The following compounds were tested and are designated in said table by the number shown to the left of their formula represented below.

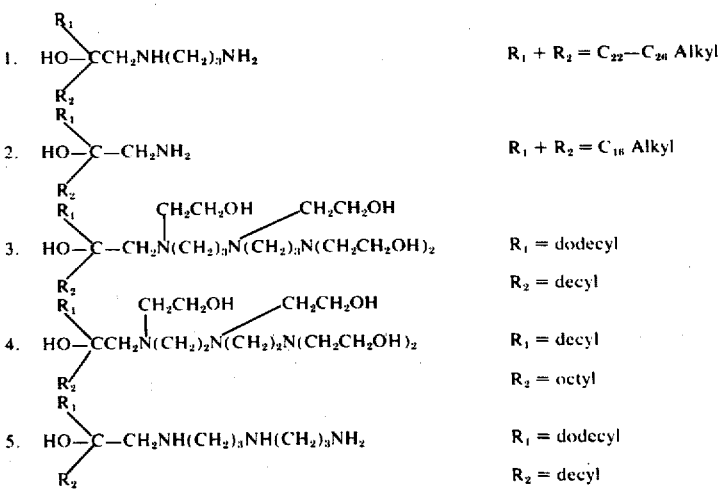

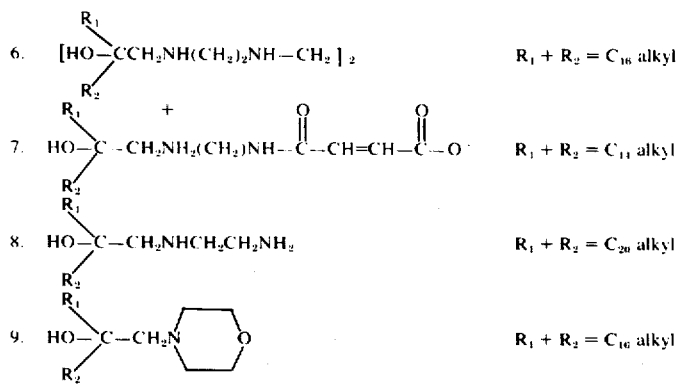

6. $[HO-\underset{R_2}{\overset{R_1}{C}}CH_2NH(CH_2)_2NH-CH_2]_2$  $R_1 + R_2 = C_{16}$ alkyl 7. $HO-\underset{R_2}{\overset{R_1}{C}}-CH_2NH_2(CH_2)NH-\overset{O}{\overset{\|}{C}}-CH=CH-\overset{O}{\overset{\|}{C}}-O^-$  $R_1 + R_2 = C_{11}$ alkyl 8. $HO-\underset{R_2}{\overset{R_1}{C}}-CH_2NHCH_2CH_2NH_2$  $R_1 + R_2 = C_{20}$ alkyl 9. $HO-\underset{R_2}{\overset{R_1}{C}}-CH_2N\overset{\frown}{\underset{\smile}{O}}$  $R_1 + R_2 = C_{16}$ alkyl

TABLE I

| Concentration (ppm) | 25 | 25 | 37.5 | 25 | 25 | 25 | 25 | 25 | 25 | |
|---|---|---|---|---|---|---|---|---|---|---|
| Temperature, °C. | 25° | 25° | 25° | 50–55° | 50–55° | 50–55° | 50–55° | 50–55° | 50–55° | (144 hrs) |
| Salt form | 0 | 0 | 0 | 0 | A | A | A | T | T | |
| Compound | | | | | % Protection | | | | | |
| 1. | 55% | 38% | 48% | 59% | 86% | 55% | 77% | | | |
| 2. | 79% | 52% | 71% | 64% | 43% | 65% | 74% | | | |
| 3. | | | | 62% | 50% | 64% | 75% | 67% | | |
| 4. | | | | | 75% | 85% | 61% | 50% | | |
| 5. | | | | | 84% | 95% | 68% | 49% | | |
| 6. | | | | | 82% | 91% | 78% | 80% | | |
| 7. | | | | | 80% | 88% | | | | |
| 8. | | | | | | | 75% | 67% | | |
| 9. | | | | | | | 54% | 65% | | |

Results comparable to those in the table are obtained using other compounds of the invention as corrosion inhibitors which are not illustrated.

EXAMPLE 18

The following example illustrates a typical preparation of an amphoteric composition. An autoclave was charged with 300 grams of 2-hexyl-1,2-epoxydecane, 150 grams of ethylenediamine, 200 grams of isopropylalcohol and 2 grams of tetraethylammonium bromide. The foregoing mixture was heated at 160°C for 2 hours. The reactor effluent was then stripped of isopropylalcohol solvent and excess amine, and filtered to give 342 grams of product containing 5.94 meq/g amine. A slurry of 22 grams of maleic anhydride in 150 ml benzene was stirred under nitrogen while 75 grams of the above prepared amine was added thereto. The mixture was heated for 1 hour at 50° to 55°C and then cooled to room temperature.

The product was precipitated by the addition of 100 ml of pentane. After two recrystallizations from benzene-pentane, 68 grams of the maleic amide, represented below, was obtained.

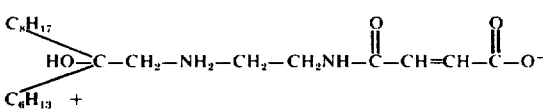

$C_8H_{17}$
$HO-\overset{}{\underset{C_6H_{13}}{C}}-CH_2-NH_2-CH_2-CH_2NH-\overset{O}{\overset{\|}{C}}-CH=CH-\overset{O}{\overset{\|}{C}}-O^-$ The preceeding examples can be repeated with similar success by substituting the generically and specifically described reactants and conditions of this invention for those employed in the examples.

As will be evident to those skilled in the art, various modifications of this invention can be made or followed in light of the discussion and disclosure herein set forth without departing from the spirit or the scope thereof.

I claim:
1. An amino alcohol having the formula:

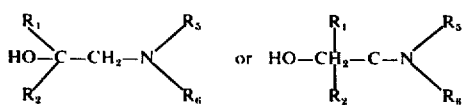

$HO-\underset{R_2}{\overset{R_1}{C}}-CH_2-N\overset{R_5}{\underset{R_6}{\diagdown}}$  or  $HO-CH_2-\underset{R_2}{\overset{R_1}{C}}-N\overset{R_5}{\underset{R_6}{\diagdown}}$ wherein, individually, $R_1$ and $R_2$ are linear $C_1$ to $C_{36}$ alkyl groups and $R_1$ and $R_2$ together contain a total of 8 to 38 carbon atoms; and wherein $R_5$ and $R_6$ individually are selected from a. alkyl, and hydroxyalkyl radicals containing from 1 to 10 carbon atoms per radical;

b. the radical

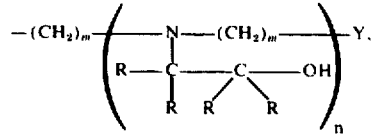

$-(CH_2)_m-\left(\underset{R-\overset{}{\underset{R'}{C}}-\overset{}{\underset{R}{C}}-OH}{N-(CH_2)_m}\right)_n-Y,$ wherein R is hydrogen or $C_1$ to $C_4$ alkyl, m is 2 or 3, n is 1 to 3, and Y is

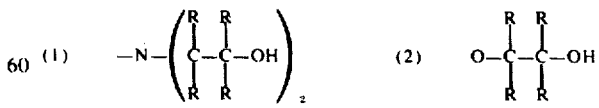

(1) $-N-\left(\underset{R\ R}{\overset{R\ R}{C-C}}-OH\right)_2$   (2) $O-\underset{R\ R}{\overset{R\ R}{C-C}}-OH$ or (3)OH
and
c. the radical

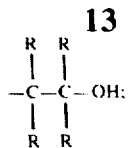
wherein R is defined as in (b); provided that at least one of $R_5$ or $R_6$ is the radical (b).
2. A compound according to claim 1 of the formula
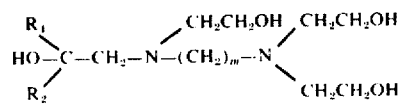
* * * * *